United States Patent [19]

Robin et al.

[11] Patent Number: 4,963,675

[45] Date of Patent: Oct. 16, 1990

[54] SUBSTANTIALLY PURE ISOCYANURATE/POLYISOCYANATES

[75] Inventors: Jean Robin, Lyons; Andre Blind, Caluire, both of France

[73] Assignee: Rhone-Poulenc Chimie, Courbevoie, France

[21] Appl. No.: 330,186

[22] Filed: Mar. 29, 1989

Related U.S. Application Data

[62] Division of Ser. No. 127,707, Dec. 2, 1987, Pat. No. 4,864,025.

[30] Foreign Application Priority Data

Dec. 2, 1986 [FR] France .................................. 86 17012

[51] Int. Cl.$^5$ .......................................... C07D 251/30
[52] U.S. Cl. ..................................... 544/222; 544/193
[58] Field of Search ................................. 544/193, 222

[56] References Cited

FOREIGN PATENT DOCUMENTS 0010589 5/1980 European Pat. Off. ............ 544/193

Primary Examiner—Mary C. Lee
Assistant Examiner—J. Richter
Attorney, Agent, or Firm—Burns, Doane, Swecker & Mathis

[57] ABSTRACT

Substantially pure isocyanurate/polyisocyanates, i.e., containing no more than about 0.03% by weight of residual diisocyanate monomer and no more than about 1% by weight of diisocyanate dimer, are produced by extracting impure cyclotrimerized diisocyanates with an inert gas in either the liquid or supercritical state.

9 Claims, No Drawings

SUBSTANTIALLY PURE ISOCYANURATE/POLYISOCYANATES

This application is a divisional of application Ser. No. 07/127,707, filed Dec. 2, 1987, now U.S. Pat. No. 4,864,025.

BACKGROUND OF THE INVENTION

1. Field of the Invention

The present invention relates to very pure polyisocyanates containing an isocyanurate moiety, and to the preparation of such isocyanurate/polyisocyanates by catalytic cyclotrimerization of aliphatic, alicyclic or arylaliphatic isocyanates.

More especially, the present invention relates to polyisocyanates containing an isocyanurate moiety which are prepared by catalytic cyclotrimerization of aliphatic, alicyclic or arylaliphatic isocyanates and which contain less than 0.03% by weight of residual isocyanate monomer and less than 1.0% by weight of dimer, based on the weight of the isocyanurate/polyisocyanate.

2. Description of the Prior Art

Many processes are known to this art for preparing polyisocyanates containing an isocyanuric group, by cyclotrimerization of isocyanates, in particular aliphatic, alicyclic or arylaliphatic diisocyanates.

These may be prepared, for example, by partial cyclotrimerization of the NCO groups of simple polyisocyanates or of polyisocyanate adducts, employing a variety of catalysts, such as tertiary amines (German Patent No. 951,168), derivatives of the alkali metals or alkaline earth metals, such as the hydroxides, carbonates or alcoholates (French Patent No. 1,190,065), quaternary ammonium hydroxides (French Patents Nos. 1,204,697 and 1,566,256; published European Patent Applications Nos. 0 3765 and 10 589), phosphines (French Patents Nos. 1,510,342 and 2,023,423), catalysts containing an ethylenimine group (French Patents Nos. 1,401,513 and 2,230,642) and Mannich bases (French Patents Nos. 2,290,459 and 2,332,274).

It is also possible to conduct this partial cyclotrimerization of NCO groups in the presence of aminosilyl compounds, such as the monoaminosilanes, diaminosilanes, silylureas and silazanes described in published European Patent Application No. 57,653.

The catalyst for the partial cyclotrimerization of NCO groups must, in general, be deactivated when the desired content of free isocyanate groups has been reached. Such deactivation may be accomplished by adding to the reaction medium an acidic compound (hydracid, acid chloride, etc.), an alkylating agent (methyl iodide, for example) or an acylating agent. This may also be accomplished by means of a suitable heat treatment.

Upon completion of the cyclotrimerization reaction, the polyisocyanate containing an isocyanurate moiety is separated by distilling off the unreacted isocyanate and, where appropriate, the solvent, when the reaction is conducted in a solvent medium.

For this purpose, it is necessary to heat the final reaction mixture, for example in an evaporator, and this permits removal of most of the residual isocyanate and, where appropriate, of the solvent. More often than not, it is then necessary to carry out an additional, more elaborate distillation in an effort to eliminate the final traces of isocyanate.

However, even after these various treatments, it is found that an amount of isocyanate at least equal to 0.1 or 0.2% by weight, based on the polyisocyanate, always remains in the final isocyanurate/polyisocyanate. In general, the polyisocyanate trimer also contains an amount of dimer equal to approximately 2 to 5% by weight based on the polyisocyanate.

In published European Patent Application No. 105,242, it has been proposed to reduce the content of residual isocyanate monomer by treating the polyisocyanate using 2 to 30% of an inert solvent, in a thin layer evaporator. This process nevertheless comprises a phase of heating the polyisocyanate to about 140° C. to 150° C., and entails the addition of a solvent which will then have to be removed.

SUMMARY OF THE INVENTION

Accordingly, a major object of the present invention is the provision of improved isocyanurate/polyisocyanates, by catalytic cyclotrimerization of at least one aliphatic, alicyclic or arylaliphatic diisocyanate in which the isocyanate groups are not directly linked to an aromatic ring, and which contain an amount of residual diisocyanate starting material of less than or equal to 0.03% by weight and an amount of dimer of less than or equal to 1% by weight, based on the said polyisocyanate.

This invention also features such isocyanurate/polyisocyanates having a content of starting material diisocyanate of less than or equal to 0.01% by weight and a content of dimer of less than or equal to 0.5%, based on the said polyisocyanate.

DETAILED DESCRIPTION OF THE PREFERRED EMBODIMENTS OF THE INVENTION

More particularly according to the present invention, exemplary of the diisocyanate monomers, the following are representative:

1,3-diisocyanatopropane,
1,4-diisocyanatobutane,
1,5-diisocyanatopentane,
1,6-diisocyanatohexane,
1,4-diisocyanato-2-ethylbutane,
1,5-diisocyanato-2-methylpentane,
1,6-diisocyanato-2,2,4-trimethylhexane,
1,6-diisocyanato-2,4,4-trimethylhexane,
1,2-diisocyanatocyclohexane,
1,4-diisocyanatocyclohexane,
1,2-bis(isocyanatomethyl)cyclobutane,
bis(4-isocyanatocyclohexyl)methane,
3,3,5-trimethyl-5-isocyanatomethyl-1-isocyanatocyclohexane,
1,4-bis(isocyanatomethyl)benzene,
1,2-bis(isocyanatomethyl)benzene.

The diisocyanate monomers may be used either alone or in the form of mixtures of two or more of them.

Thus, for example, 1,6-diisocyanatohexane, which is one of the preferred diisocyanate monomers, may be used alone or mixed, in particular, with 1,5-diisocyanato-2-methylpentane and/or 1,4-diisocyanato-2-ethylbutane; mixtures of the latter two diisocyanates can also be used.

The final product isocyanurate/polyisocyanates are useful, in particular, for preparing non-yellowing polyurethane paints and varnishes. Since the free diisocyanates are relatively toxic, it is especially advantageous to have available polyisocyanates containing an isocyanurate moiety in which the residual diisocyanate level is very low. Furthermore, the dimer of the starting isocyanate, which is formed in greater or lesser amount during the cyclotrimerization reaction, is capable, under certain heating conditions, of partially regenerating free diisocyanate. This risk is virtually eliminated when isocyanurate/polyisocyanates are available having a low content of dimer.

This invention also features a simple and efficient process for producing the subject isocyanurate/polyisocyanates having low contents of residual diisocyanate and the dimer thereof, by extracting, after completion of the cyclotrimerization reaction, the excess diisocyanate monomer and the dimer formed, using an inert gas in the liquid state or in the supercritical state.

Exemplary of the inert gases, carbon dioxide, butane, ethane, propane and ethylene are representative.

Carbon dioxide, which is cheap, non-toxic and non-flammable, is the most preferred compound, either in the liquid or supercritical state.

The extraction may be carried out in continuous or discontinuous fashion.

In the liquid state, the carbon dioxide is typically employed at a temperature of from 0° C. to 31° C. and under a pressure of 30 to 500 bars.

It is preferable to conduct the operation at from 20° C. to 31° C., in order that the viscosity of the polyisocyanate to be treated should not be too great, and under a pressure of 60 to 300 bars.

In the supercritical state, the temperature is above the critical temperature of carbon dioxide (31.4° C.) and the pressure typically ranges from 73 to 500 bars. Preferably, the pressure ranges from 73 to 350 bars and the temperature from 31.4° C. to 100° C.

It is possible to treat the reaction mass from the completion of the cyclotrimerization reaction forwards.

However, in light of the large excess amounts of diisocyanate monomer, it may be preferable and more economical to perform a prior rapid removal of most of the excess diisocyanate monomer.

This treatment, which is frequently a very rapid evaporation under reduced pressure, does not require the reaction mass to be heated to a high temperature.

Hence, in practice, the mass obtained after the cyclotrimerization reaction is transferred to a thin film evaporator, which enables approximately 80 to 90% of the excess diisocyanate monomer to be separated.

The isocyanurate/polyisocyanate, still containing a relatively large amount of diisocyanate monomer, is then treated using, e.g., the liquid $CO_2$ or $CO_2$ in the supercritical state.

It is possible to conduct the operation in discontinuous fashion, for example, by mixing the isocyanurate/polyisocyanate sought to be purified with the liquid carbon dioxide or carbon dioxide in the supercritical state, in a suitable reactor.

After separation of the carbon dioxide (containing the diisocyanate monomer and the dimer) from the purified isocyanurate/polyisocyanate, it is possible to separate said carbon dioxide from the extracts by releasing the pressure and/or increasing the temperature.

The extraction may be carried out in the conventional manner, in an apparatus known per se.

From a carbon dioxide source, the said gas is transferred to a heat exchanger where it is liquified; it is then conveyed, at the desired pressure, by means of a pump, to another heat exchanger in which its temperature is adjusted to the temperature selected for the extraction.

The carbon dioxide, in the liquid state or in the supercritical state, is then transferred to the extraction apparatus, which can be, for example, a packed column permitting better contact between the isocyanurate/polyisocyanate and the carbon dioxide.

The isocyanurate/polyisocyanate can be introduced at the other end of the column, constituting a countercurrent extraction. Less frequently, it can be introduced at the same end as the extraction gas, constituting a cocurrent extraction.

The purified isocyanurate/polyisocyanate is recovered at one end of the extraction column, while the carbon dioxide, charged with diisocyanate monomer, the dimer of this diisocyanate and trace polyisocyanate, is treated in order to separate it from the extracted compounds.

Since the carbon dioxide extracts a certain amount of isocyanurate/polyisocyanate, it is advantageous, in practice, to recover the major part of this polyisocyanate. For this purpose, it is possible to perform a fractional separation of the extracts, by modifying the solvent power of the carbon dioxide containing the extracts. The isocyanurate/polyisocyanate, which is less soluble than the diisocyanate and the dimer, may thus be separated. This modification of the solvent power of the carbon dioxide can be achieved by decreasing its pressure, or most typically by increasing its temperature.

The carbon dioxide, charged principally with diisocyanate and dimer, is then treated to separate it from these extracted compounds.

As aforesaid relative to the isocyanurate/polyisocyanate, it is possible to achieve this either by decreasing its pressure or by increasing its temperature.

This decrease, or release of pressure, may be carried out in one or more stages, and the pressure of the carbon dioxide may be relaxed to a value equal to atmospheric pressure, or to a higher pressure, under which it will be recycled in the event that a continuous process is employed.

In effect, if the carbon dioxide is recycled, it is economically preferable not to release its pressure to atmospheric pressure, which would require a larger expenditure of energy in order to recompress it in the following cycle of the process. It is preferable to relax it only to a pressure under which the extracted compounds are insoluble, or only very slightly soluble.

It is also possible to separate the carbon dioxide from the extracts as a whole which it contains, as described above, and subject this mixture of extracts, comprising the diisocyanate monomer, the dimer and the extracted fraction of trimer containing an isocyanuric group, to a further extraction with carbon dioxide in the liquid or supercritical state. This second extraction, conducted on a mixture that is much less rich in isocyanurate/polyisocyanate than the mixture derived from the cyclotrimerization process, loses much less trimer.

It too is possible to recycle the extracts as a whole, comprising the diisocyanate monomer, the dimer and the extracted portion of trimer, into the phase of preparation of the isocyanurate trimer. The concentration of the product with respect to dimer will increase in proportion to the recycling steps: after a certain number of recycling steps, it is then possible to proceed, according to one of the above embodiments, to the separation of the dimer and the diisocyanate monomer from the extracted portion of the isocyanurate trimer.

As stated above, the process may be carried out in continuous or discontinuous fashion, and the apparatus used is not limited to that actually described above.

In general, it is preferred to use carbon dioxide in the supercritical state.

In order to further illustrate the present invention and the advantages thereof, the following specific examples are given, it being understood that same are intended only as illustrative and in nowise limitative.

EXAMPLE 1

90.8 g of isocyanurate trimer, prepared from 1,6-diisocyanatohexane (HDI), were introduced into a stainless steel column 19 mm in diameter and 250 mm high, packed with Dixon packing. This polyisocyanate contained 4.3% by weight of free HDI and approximately 2.5% by weight of dimer.

The column was thermostatted at 20° C. Carbon dioxide was admitted, in the liquid state, to a pressure of 100 bars.

The pressure to which the extraction column was relaxed was maintained at the desired value by means of a pressure regulator.

When the system was at equilibrium, carbon dioxide in the liquid state was charged through the base of the column at a flow rate of approximately 800 g/hour.

The extracts were recovered on the distant side of the pressure regulator by relaxation to atmospheric pressure in a succession of bottles.

The HDI content of the treated polyisocyanate was monitored by liquid chromatography.

Table I below reports the results of the experiment:
(i) Amount of extract (HDI+dimer+trimer);
(ii) Ratio by weight extract/polyisocyanate charged;
(iii) Content of HDI in the treated polyisocyanate, in terms of the amount of liquid $CO_2$ employed;
(iv) Content of dimer in the treated polyisocyanate, in terms of the amount of liquid $CO_2$ employed.

TABLE I

| Cumulative weight of liquid $CO_2$ employed | Cumulative weight of extract | Extract/ polyisocyanate charged, % by wt. | Content of HDI, % by wt. | Content of dimer, % by wt. |
| --- | --- | --- | --- | --- |
| 500 g | 5.4 g | 6.0 | 0.32 | 1.2 |
| 1000 g | 7.8 g | 8.6 | 0.06 | 1.1 |
| 1500 g | 9.45 g | 10.4 | 0.008 | 0.7 |
| 2500 g | 10.8 g | 11.9 | 0.005 | 0.5 |

EXAMPLE 2

20.1 g of isocyanurate trimer, prepared from HDI, were introduced into a 45-cm³ autoclave incorporating two glass inspection windows. This polyisocyanate contained 0.18% of free HDI and approximately 2.5% by weight of dimer.

The autoclave was thermostatted at 35° C. Carbon dioxide was admitted in the supercritical state to a pressure of 100 bars. The pressure to which the autoclave was relaxed was maintained at the desired value by means of a pressure regulator.

When the system was at equilibrium, carbon dioxide in the supercritical state was charged through the base of the autoclave at a flow rate of approximately 700 g/hour.

The extracts were recovered under the conditions described in Example 1.

The results obtained are reported below:

(i) Weight of supercritical $CO_2$ employed: 5,000 g;
(ii) Weight of extract: 2.2 g;
(iii) Extract/polyisocyanate charged (% by weight): 10.95;
(iv) Content of HDI in the treated polyisocyanate (% by weight): 0.005%;
(v) Content of dimer in the treated polyisocyanate (% by weight): 0.4%.

EXAMPLE 3

This example illustrates a continuous operation according to the invention.

The apparatus used consisted of:
(i) a stainless steel extraction column 1 meter long having an internal diameter of 16 mm, filled with 3 mm×3 mm stainless steel DIXON rings (this column incorporated a jacket for the circulation of the heating fluid); (ii) a pump for feeding the HDI trimer to be treated, at the top of the column; (iii) a pump for feeding carbon dioxide at the base of the column; and (iv) a column for extraction of purified trimer.

The HDI trimer containing 1.1% by weight of free HDI was injected into the top of the column, which was thermostatted at 40° C. The trimer was preheated upstream of the feed pump.

It was injected at a flow rate of 130 grams/hour, while supercritical $CO_2$ was injected into the base of the column (40° C., 200 bars) at a flow rate of 2,600 g/hour.

The experiment was continued for 5 hours, operating in continuous fashion.

The purified HDI trimer was drawn off in continuous fashion at the rate of 110 g/hour.

The purified trimer contained 0.003% of free HDI.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for purifying a cyclotrimerized diisocyanate comprising an isocyanurate/polyisocyanate, said isocyanurate/polyisocyanate containing no more than about 0.03% by weight of residual diisocyanate monomer and no more than about 1% by weight of diisocyanate dimer, comprising extracting diisocyanate monomer and diisocyanate dimer from a cyclotrimerized diisocyanate comprising at least 0.1% by weight of diisocyanate monomer and at least 2% of diisocyanate dimer, with an inert gas in either the liquid or supercritical state, said inert gas being capable of extracting diisocyanate monomer and diisocyanate dimer.

2. The process as defined by claim 1, said inert gas comprising carbon dioxide in either liquid or supercritical state.

3. The process as defined by claim 2, carried out at a temperature of from 0° to 31° C. and under a pressure of 30 to 500 bars.

4. The process as defined by claim 3, carried out at a temperature of from 20° to 31° C. and under a pressure of 60 to 300 bars.

5. The process as defined by claim 2, carried out at a temperature above the critical temperature of carbon dioxide, and under a pressure of 73 to 500 bars.

6. The process as defined by claim 1, comprising removing excess diisocyanate monomer upstream of the extraction with the inert gas in the liquid or supercritical state.

7. The process as defined by claim 2, comprising recovering the isocyanurate/polyisocyanate, dissolved in carbon dioxide, and then separating the carbon dioxide, on the one hand, and diisocyanate and dimer on the other, by decreasing the pressure and/or increasing the temperature of the carbon dioxide.

8. The process as defined by claim 5, carried out at a temperature of from 31.4° to 100° C. and under a pressure of 73 to 350 bars.

9. The process as defined by claim 1, said inert gas comprising carbon dioxide, butane, ethane, propane or ethylene, in either the liquid or supercritical state.

* * * * *